(12) United States Patent
Godefroy et al.

(10) Patent No.: US 8,512,977 B2
(45) Date of Patent: Aug. 20, 2013

(54) ANALYZING RETICULOCYTES

(75) Inventors: Christophe P. Godefroy, Miramar, FL (US); John Steven Riley, Miami, FL (US); Patricio J. Vidal, Miami, FL (US)

(73) Assignee: Beckman Coulter, Inc.

( * ) Notice: Subject to any disclaimer, the term of this patent is extended or adjusted under 35 U.S.C. 154(b) by 856 days.

(21) Appl. No.: 12/234,275

(22) Filed: Sep. 19, 2008

(65) Prior Publication Data

US 2010/0075369 A1    Mar. 25, 2010

(51) Int. Cl.
  *C12Q 1/06* (2006.01)
(52) U.S. Cl.
  USPC ............................................. 435/39; 435/34
(58) Field of Classification Search
  USPC ...................................................... 435/34, 39
  See application file for complete search history.

(56) References Cited

U.S. PATENT DOCUMENTS

| | | | | |
|---|---|---|---|---|
| 5,492,833 | A | * | 2/1996 | Rodriguez et al. ............... 436/63 |
| 5,616,501 | A | | 4/1997 | Rodriguez et al. |
| 6,060,322 | A | | 5/2000 | Horton et al. |
| 6,410,330 | B1 | | 6/2002 | Li et al. |
| 6,472,215 | B1 | | 10/2002 | Huo et al. |
| 2004/0132196 | A1 | | 7/2004 | Mizukami et al. |

OTHER PUBLICATIONS

Beckman Coulter, "Coluter® 3-D VCS Technology," available online at http://www.beckmancoulter.com/products/instrument/hematology/VCS_Technology.pdf.(accessed Jun. 2008).
Kessler, C., et al., "Immature Reticulocyte Fraction and Reticulocyte Maturity Index," available online at http://www.beckmancoulter.com/listerature/ClinDiag/recticliterature.pdf (accessed Jun. 2008).
Prahl, S., "Optical Absorption of Hemoglobin," available online at http://omlc.ogi.edu/spectra/hemoglobin/index (accessed Jan. 2000).

* cited by examiner

*Primary Examiner* — Jon P Weber
*Assistant Examiner* — Robert Yamasaki
(74) *Attorney, Agent, or Firm* — K&L Gates LLP; Louis C. Cullman (57) ABSTRACT

Methods, systems, and computer program products for the analysis of particle analyzer data are disclosed. One embodiment is a method of analyzing immature reticulocytes in a blood sample, including the steps of: preprocessing the blood sample; measuring the blood sample by a detection including a reticulocyte-maturity measurement and a light scatter measurement; analyzing blood cell distribution patterns to identify a set of reticulocyte events; differentiating immature reticulocytes from mature reticulocytes using the reticulocyte-maturity measurement and the light scatter measurement; and reporting immature reticulocytes. The immature reticulocyte fraction may be one aspect that is reported. Also another method is disclosed, having the steps of: measuring the blood sample by a detection comprising an axial light loss measurement; identifying a hard-to-ghost cell population based on the axial light loss measurement; filtering-out the hard-to-ghost cell population; and analyzing the event data to identify blood cell distribution patterns.

12 Claims, 12 Drawing Sheets

ANALYZING RETICULOCYTES

BACKGROUND OF THE INVENTION

1. Field of the Invention

This invention relates in general to the analysis of blood samples using a particle analyzer, and more particularly to determining reticulocytes.

2. Background

The predominant cell in blood is the erythrocyte, i.e., red blood cell or red cell. In a peripheral blood smear, erythrocytes derive their reddish color from protein hemoglobin, and usually appear round or oval with a pale-staining center region. Their biconcave morphology increases the cell's surface area and facilitates diffusion of oxygen and carbon-dioxide from the cell. A typical erythrocyte has a lifespan of about 120 days.

Erythrocytes develop from nucleated precursor cells in the bone marrow. Immature erythrocytes, i.e., reticulocytes, have organelles that contribute to an increased hemoglobin content and gas-carrying capacity. Reticulocytes may be recognized in peripheral blood smears when a special stain is used to stain their polyribosome or ribonucleic acid (RNA). Under typical conditions, reticulocytes account for about 1-2% of red blood cells in a sample. However, during certain periods of physical need, the reticulocyte count may increase.

The RNA of a reticulocyte degrades and reduces in size over a period of days. Immature reticulocytes are larger and contain a greater quantity of RNA. A measure of reticulocyte maturation can provide an increased understanding of erythrocyte activity.

For example, the immature reticulocyte fraction (IRF), i.e., ratio of immature reticulocytes to total reticulocytes, can be useful in many aspects including evaluating the extent of bone marrow suppression during chemotherapy, monitoring bone marrow engraftment, assessing neonatal transfusion needs, etc.

Automated reticulocyte analysis is done using a particle analyzer such as a flow cytometer or hematology analyzer. Example particle analyzers include, the Gen•S™ System from Beckman Coulter and XT-2000 from Sysmex Corporation. The preparation of a blood sample for flow cytometric or hematology analysis generally involves, taking a whole blood sample and performing one or both the steps of, incubating the sample of blood with a vital stain such as New Methylene Blue (NMB), and diluting the blood sample with a hypotonic acid that clears hemoglobin. The staining precipitates RNA within the erythrocytes. Diluting with a hypotonic acid clears hemoglobin, leaving the stained RNA within the cells. The process of removing hemoglobin is commonly referred to as "ghosting." The blood sample, or portion of it, is then subjected to analysis in a flow cell of a particle analyzer. Typically, cells in a sheath fluid pass through a point in the flow cell, one by one, where they are interrogated by probes including one or more beams of light. Several measurements are generated for each passing cell. The interrogation of a single cell is referred to as a cell event. Commonly recorded measurements per cell event include, forward light scatter, side scatter, axial light loss, and fluorescence. Some particle analyzers also collect a direct current impedance (DC) measurement which is a measure of how much impedance is exerted by a cell. The DC measurement, which is obtained from applying the maximum current such that the cell membrane is not permeated and no current flows through the cell, is also known as Coulter volume or volume.

Younger erythrocytes have a larger quantity of RNA that cause a higher amount of light to be scattered than from the more mature erythrocytes. For example, light scatter measurements such as side scatter are generally proportional to the number of nucleic granules. Also, the reticulocytes are generally larger than the mature erythrocytes because they have a larger quantity of RNA granules. Other light scatter measurements may also be used to measure the maturity of the cells. For example, a measurement such as forward scatter or fluorescence also indicates the relative amount of RNA in each cell. In addition, the volume of a cell can be directly measured through the DC measurement.

Current reticulocyte analysis methods, in general, use only one measurement indicative of reticulocyte maturity to differentiate reticulocytes. For example, C. Kessler, P. Campbell, V. Bolufe, I. Fernandez, "Immature Reticulocyte Fraction and Reticulocyte Maturity Index", www.beckmancoulter.com/literature/ClinDiag/recticliterature.pdf (last accessed Jun. 30, 2008), describes a method in which light scatter and volume measurements are used to differentiate reticulocytes from mature red cells, and the light scatter by itself being used for differentiating the reticulocytes according to maturity. As another example, U.S. Patent Publication No. 2004/0132196 describes a method in which fluorescence and forward scatter are used to differentiate reticulocytes from mature red cells, and fluorescence by itself being used for differentiating the reticulocytes according to maturity. The use of a second measurement that is indicative of reticulocyte maturity, may help increase the efficiency and accuracy of reticulocyte analysis.

Therefore, what are needed are methods and systems to more accurately measure reticulocyte populations.

BRIEF SUMMARY OF THE INVENTION

The present invention is directed towards the analysis of particle analyzer data. In one embodiment, a method of analyzing immature reticulocytes in a blood sample is presented, that includes the steps of: preprocessing the blood sample for analysis in a flow cell; measuring the blood sample in the flow cell by a detection including a reticulocyte-maturity measurement and a light scatter measurement to generate event data; analyzing blood cell distribution patterns from said event data to identify a set of reticulocyte events corresponding to a population of reticulocytes; differentiating immature reticulocytes from mature reticulocytes using the reticulocyte-maturity measurement and the light scatter measurement; and reporting immature reticulocytes in the blood sample. An example of an aspect that is reported may be the immature reticulocyte fraction.

In another embodiment a method of analyzing a blood sample can include the steps of: measuring the blood sample in a flow cell by a detection comprising an axial light loss measurement to generate event data; identifying a hard-to-ghost cell population using the event data, based on the axial light loss measurement; filtering-out the hard-to-ghost cell population from said event data; and analyzing the event data to identify blood cell distribution patterns. Subsequent to filtering out the hard-to-ghost cells analysis including the reticulocyte analysis can be performed.

In another embodiment, the present invention is an apparatus for analyzing a blood sample, having as components: a particle analyzer; a reticulocyte module, and; a display device. The reticulocyte module includes: a first module that enables measuring the blood sample in a flow cell by a detection comprising a reticulocyte-maturity measurement and a light scatter measurement; a second module that enables analyzing blood cell distribution patterns obtained from measuring said sample to identify a set of events corresponding to a population of reticulocytes; a third module that enables differentiating immature reticulocytes from mature reticulocytes using the reticulocyte-maturity measurement and the light scatter measurement; and a fourth module that enables reporting immature reticulocytes in the blood sample.

In yet another embodiment, the present invention is a computer program product causing a computer to analyze a blood sample using a flow cytometer by: a first computer readable program code that enables measuring the blood sample in a flow cell by a detection comprising a reticulocyte-maturity measurement and a light scatter measurement; a second computer readable program code that enables analyzing blood cell distribution patterns obtained from measuring said blood sample to identify a set of reticulocyte events corresponding to a population of reticulocytes; a third computer readable program code that enables differentiating immature reticulocytes from mature reticulocytes using the reticulocyte-maturity measurement and the light scatter measurement; and a fourth computer readable program code that enables reporting immature reticulocytes in the blood sample.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION OF THE INVENTION

The present invention relates to particle analysis data processing. While the present invention is described herein with reference to illustrative embodiments for particular applications, it should be understood that the invention is not limited thereto. Those skilled in the art with access to the teachings herein will recognize additional modifications, applications, and embodiments within the scope thereof and additional fields in which the invention would be of significant utility.

Overview

As described in the background section above, the ability to determine the proportion and quality of reticulocytes in a blood sample is a vital capability for several applications. A measure of reticulocyte maturation, for example, through a quantification such as the immature reticulocyte fraction, can provide an increased understanding of erythocytic activity.

The methods and systems disclosed herein yield an improved measure of immature reticulocytes in a blood sample. In one embodiment of the present invention, the immature reticulocytes are determined using at least two measurements that are variable according to reticulocyte maturity. The use of multiple measurements that are dependent on reticulocyte maturity provide for a more accurate differentiation of immature reticulocytes from mature reticulocytes. Another embodiment of the present invention is a method where more of the cells that should have been initially ghosted are removed from the data sample, thereby further improving the accuracy of all subsequent reticulocyte analysis using the data sample.

Exemplary environments in which this invention may be practiced include flow cytometers and hematology analyzers, such as Beckman Coulter's Gen•S™ System. The Gen•S™ System, for example, uses the Coulter proprietary Volume, Conductivity, and Scatter (VCS) technology to probe hydrodynamically focused cells within a flow cell. VCS uses three independent energy sources that work in concert with each other to probe cells: a low frequency direct current power source to measure volume; a high frequency power source to measure conductivity, and a laser light source to measure scatter. The volume measurement is performed using the Coulter principle of electrical impedance to physically measure the volume that the entire cell displaces in an isotonic diluent. This method accurately sizes all cell types regardless of their orientation in the light path. Alternating current in the radio frequency (RF) range short circuits the bipolar lipid layer of a cell's membrane, allowing the energy to penetrate the cell. This powerful probe is used to collect information about cell size and internal structure, including chemical composition and nuclear volume. A laser and multiple-angle light scatter detectors provide information about a cell's internal structure, granularity, and surface morphology. In addition, VCS devices use the highly accurate DC measurement of volume, to obtain other measurements that are adjusted for cell size from conductivity and scatter. U.S. Pat. No. 5,616,501 (to Rodriguez et. al), U.S. Pat. No. 6,060,322 (to Horton et. al), U.S. Pat. No. 6,410,330 (to Li et. al), and U.S. Pat. No. 6,472,215 (to Huo et. al), all of which are hereby incorporated by reference in their entirety, describe the use of VCS technology with respect to detecting reticulocytes and other reticulated cells. It should be noted, however, that the teachings in this disclosure are not limited to devices using VCS technology.

Figure 1:
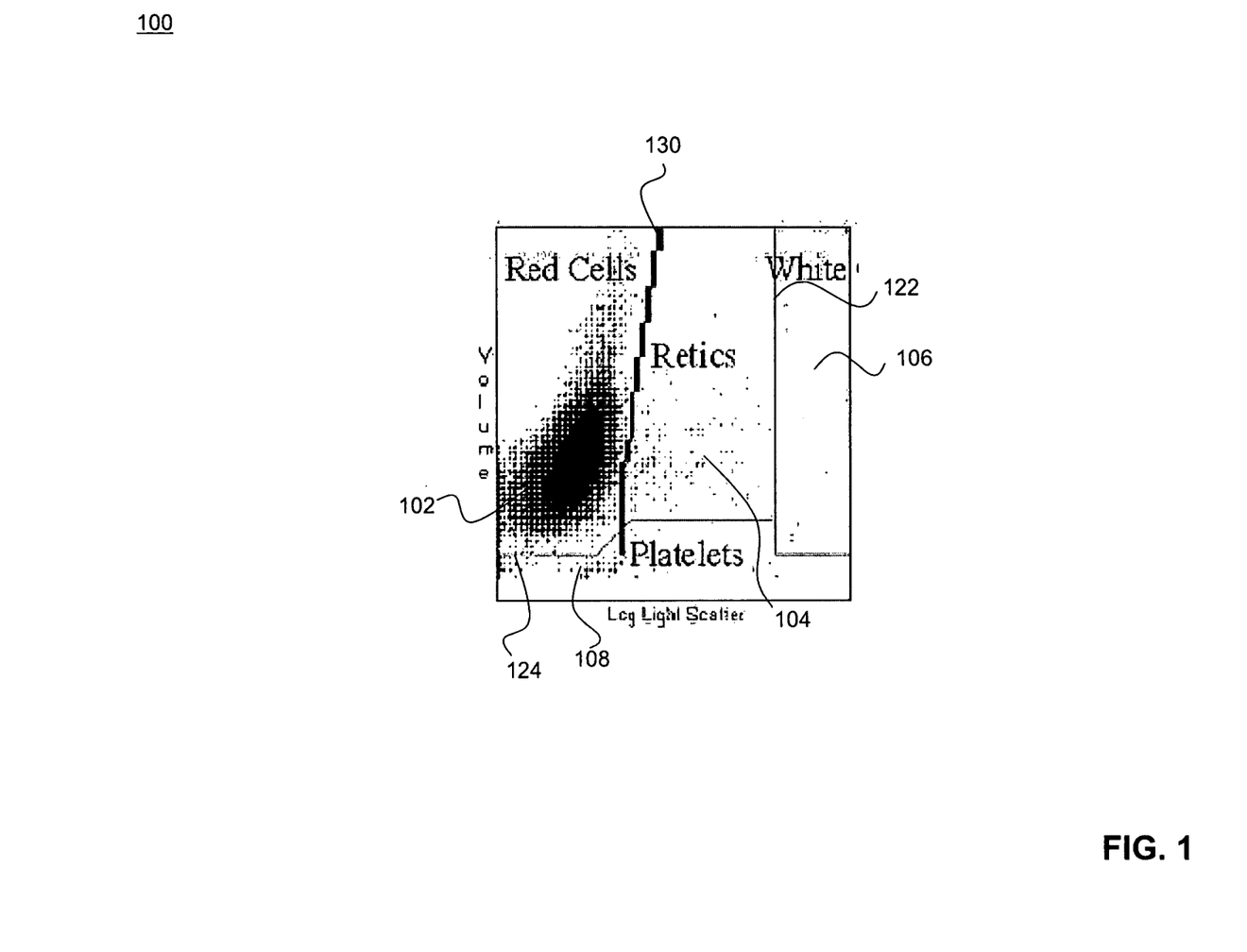
FIG. 1 is a view of event data from analysis of a blood sample using a flow cytometer, in two-dimensions.

FIG. 1 shows a two-dimensional scatter plot 100 of a blood sample based on event data generated from measurements of blood using a particle analyzer. Each data point appearing in the scatter plot 100 is based on selected measurements obtained from one cell event, i.e., the interrogation of an individual cell by probes in the flow cell. Event data populations of different cell types commonly found in a blood sample are shown in scatter plot 100. In general, sufficient separation exists between the populations of red cells as a whole (i.e., erythrocytes 102 and reticulocytes 104), platelets 108, and white cells 106, that known techniques allow for gating the red cell population as a whole, for example, based on the area defined by lines 122 and 124. Gating refers to the process of filtering selected measurements from multi-parameter data, for example, as described above, separating red cells (erythrocytes and reticulocytes), platelets and white blood cells by testing the measurements generated for each cell event against known threshold values. For example, line 124 may be a threshold volume value and line 122 may be a threshold light scatter value, where cell events with volume measurements above line 124 and light scatter (often used in the form of log of light scatter) value less than line 122 correspond to either erythrocytes or reticulocytes. In existing systems, the reticulocyte population can also be gated, for example, by a line such as line 130. The events to the right of line 130 are reticulocytes, whereas the events to the left of line 130 are mature red cells.

Figure 2:
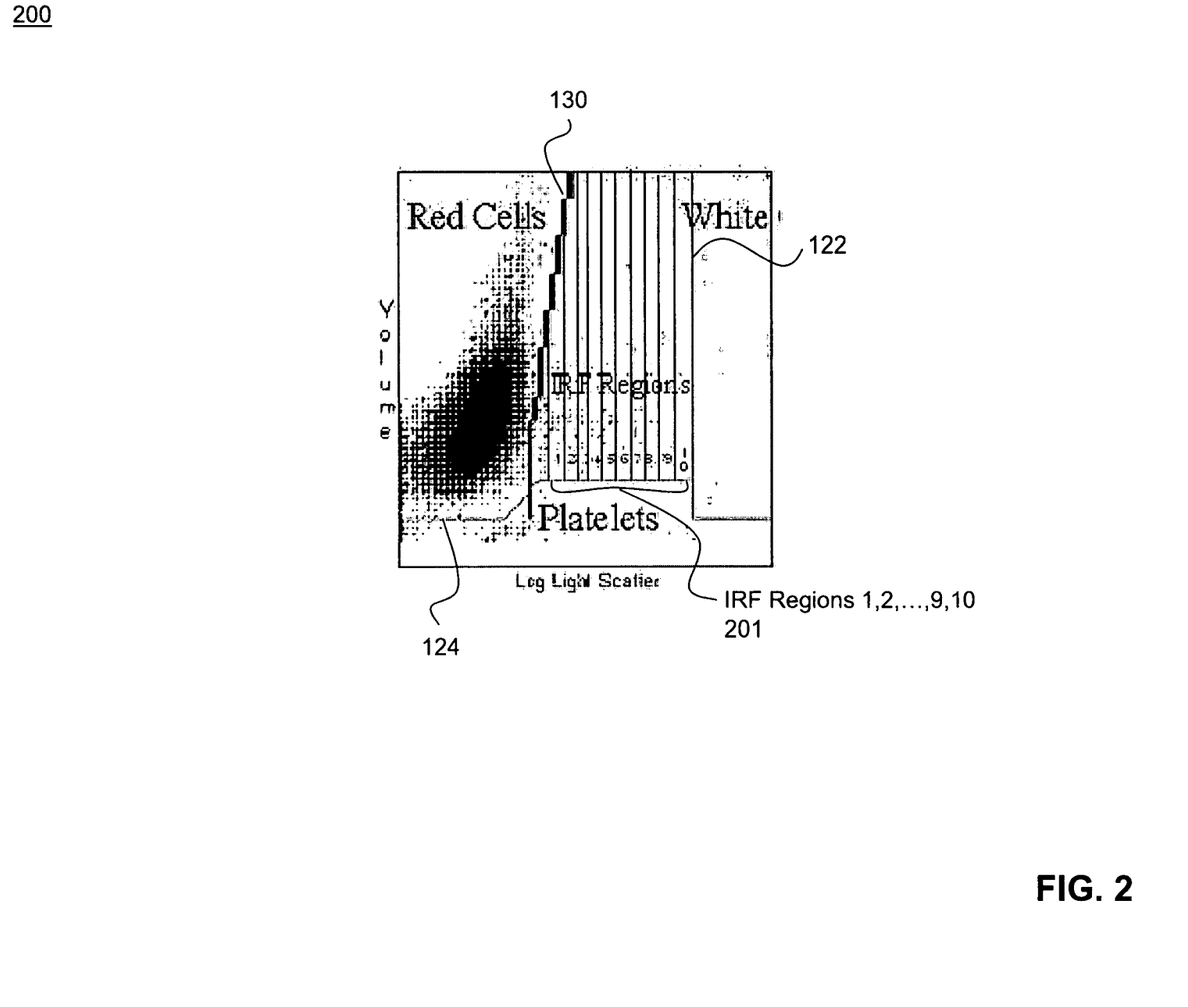
FIG. 2 shows a part of a known method of evaluating immature reticulocytes.

The scatter plot 200 of FIG. 2 illustrates a method used in existing systems, for example, in Beckman Coulter's Gen•S™ System, to differentiate reticulocytes according to their maturity. Differentiating immature reticulocytes from the mature reticulocytes involves classifying reticulocytes according to their maturity. In 200, the area having the reticulocyte population (reticulocyte events), i.e., the area defined by lines 122, 124 and 130, is divided into a predefined number, here 10, of regions (i.e., immature reticulocyte fraction regions) 201 along the x-axis. In 200, the x-axis represents the log of the light scatter measurement. The events in each region are aggregated, and the immature reticulocyte fraction (IRF) is returned as, for example, the ratio of the aggregated events in the 8 leftmost regions, to the total reticulocyte events. The light scatter emitted by immature reticulocytes increase with their level of immaturity, and hence the consideration of the right most regions to represent the most immature reticulocytes for the comparison.

Evaluating Reticulocyte Maturity

Figure 3:
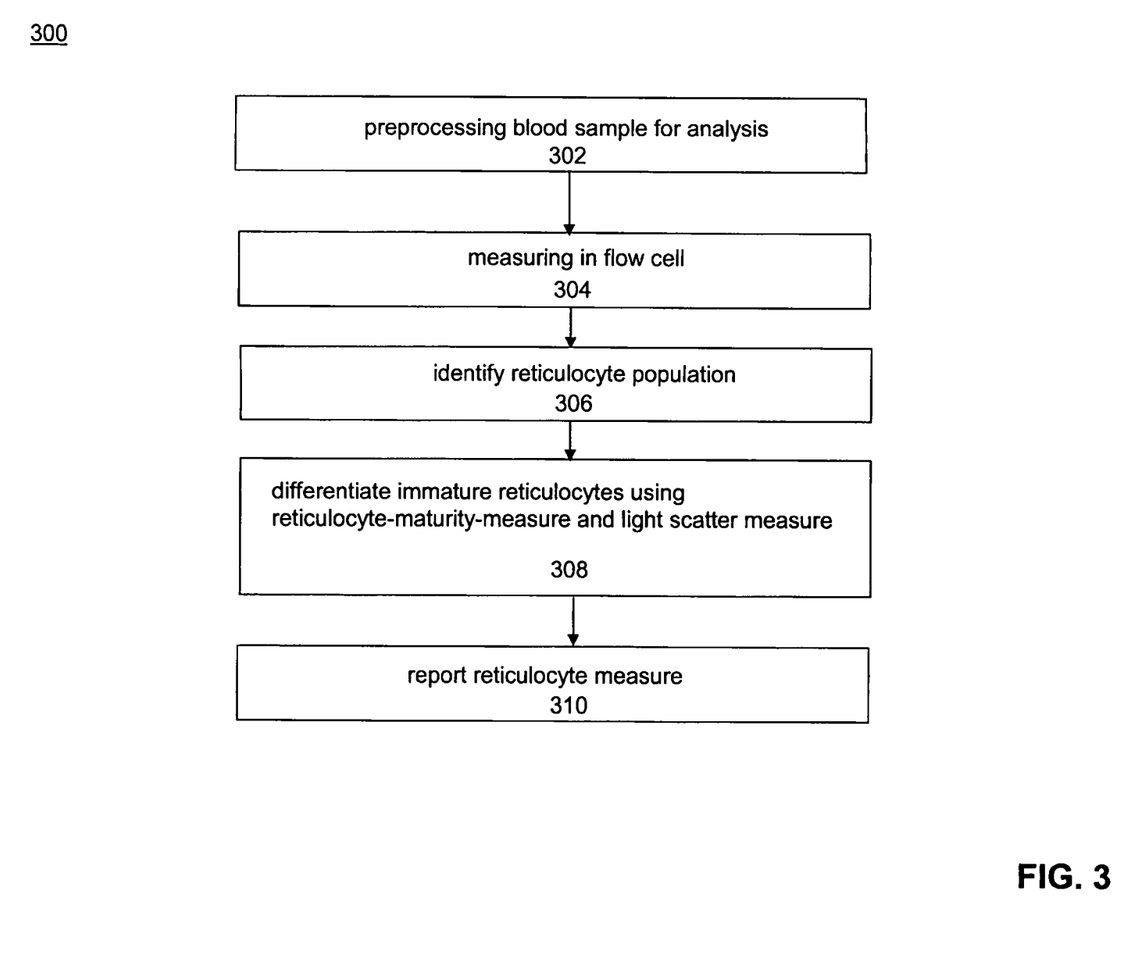
FIG. 3 illustrates steps in analyzing immature reticulocytes in a blood sample according to an embodiment of the present invention.
Figure 4:
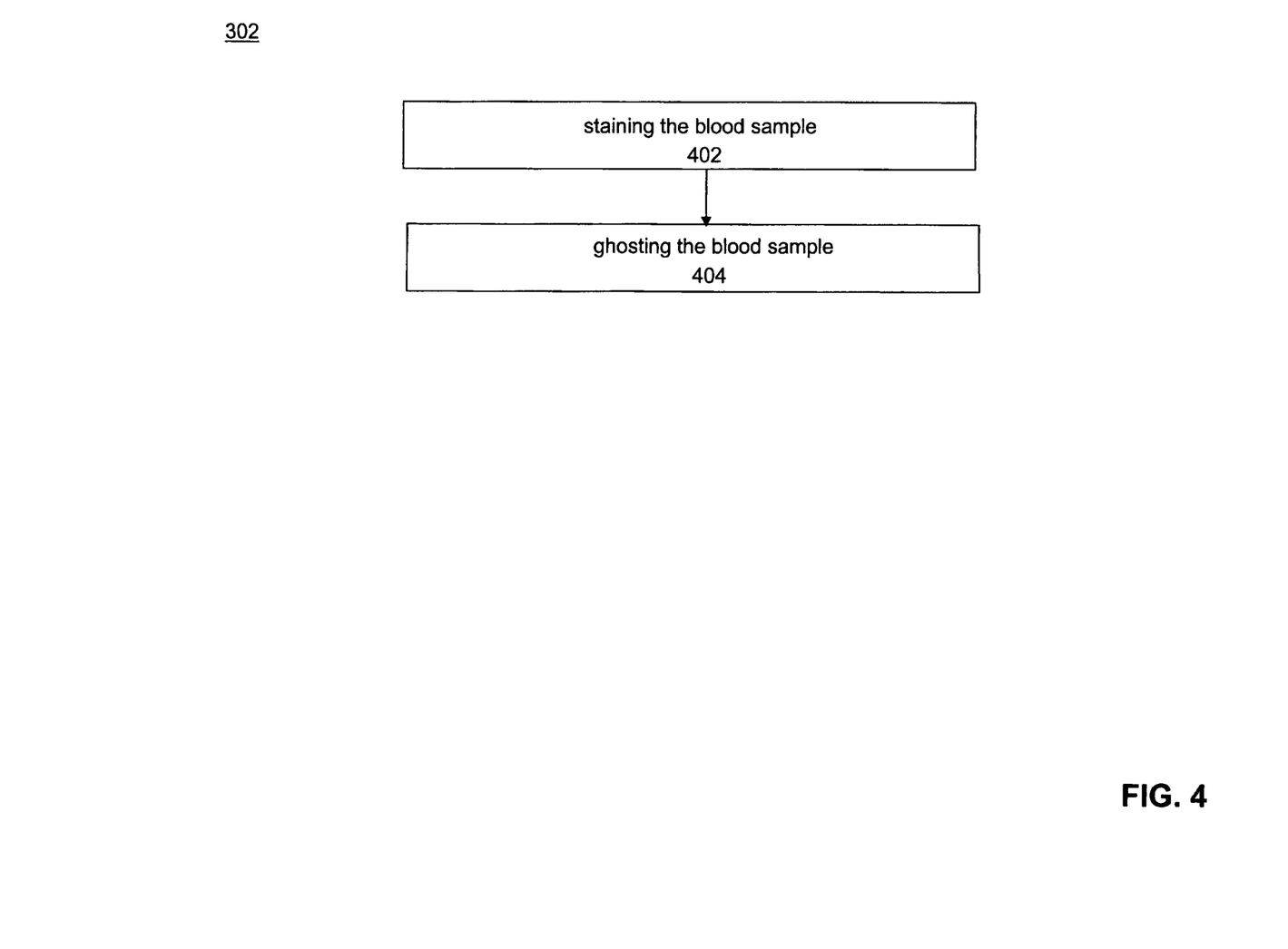
FIG. 4 shows further details of the preprocessing step shown in FIG. 3, according to an embodiment of the present invention.

FIG. 3 is a flowchart 300 of steps in evaluating reticulocytes according to an embodiment of the present invention. In step 302, a blood sample is prepared for analysis in a particle analyzer. Preparation may include ghosting the blood sample and/or staining the sample with a suitable dye or stain. FIG. 4 illustrates preparation step 302 in further detail, according to an embodiment of the present invention. In step 402, the blood sample may be combined with a vital stain to further delineate reticulocytes. For example, a non-fluorochrome dye that precipitates intracellular ribonucleic acid (RNA) of the reticulocyte may be used. Examples of suitable stains include, but are not limited to, New Methylene Blue, Oxazine 750, and Brilliant Cresyl Blue. RNA, having been stained, will have fluorescing characteristics that enhances the delineation of the RNA content in each cell. Using a non-fluorescent dye to measure reticulocytes allows the blood sample to be further analyzed for other constituents by utilizing a fluorescent dye. In step 404, the blood sample can be combined with a reagent such as, for example, a reticulocyte ghosting solution having potassium thiocyanate and sulfuric acid. The ghosting process releases the hemoglobin in red blood cells. The reduction of the hemoglobin content enhances the definition of the reticulum to permit flow cytometric determination of the reticulocytes. In addition to facilitating the release of hemoglobin, the ghosting process may also sphere the red blood cells giving the cells a more regular shape, and thereby permitting more predictable light scatter measurements. See, e.g., U.S. Pat. No. 6,060,322, incorporated by reference above. Additional preparatory steps are possible in various embodiments of the present invention. For example, in some embodiments a fluorescent dye may be combined with the blood sample to measure additional properties of the sample using a fluorescence measure.

Figure 5:
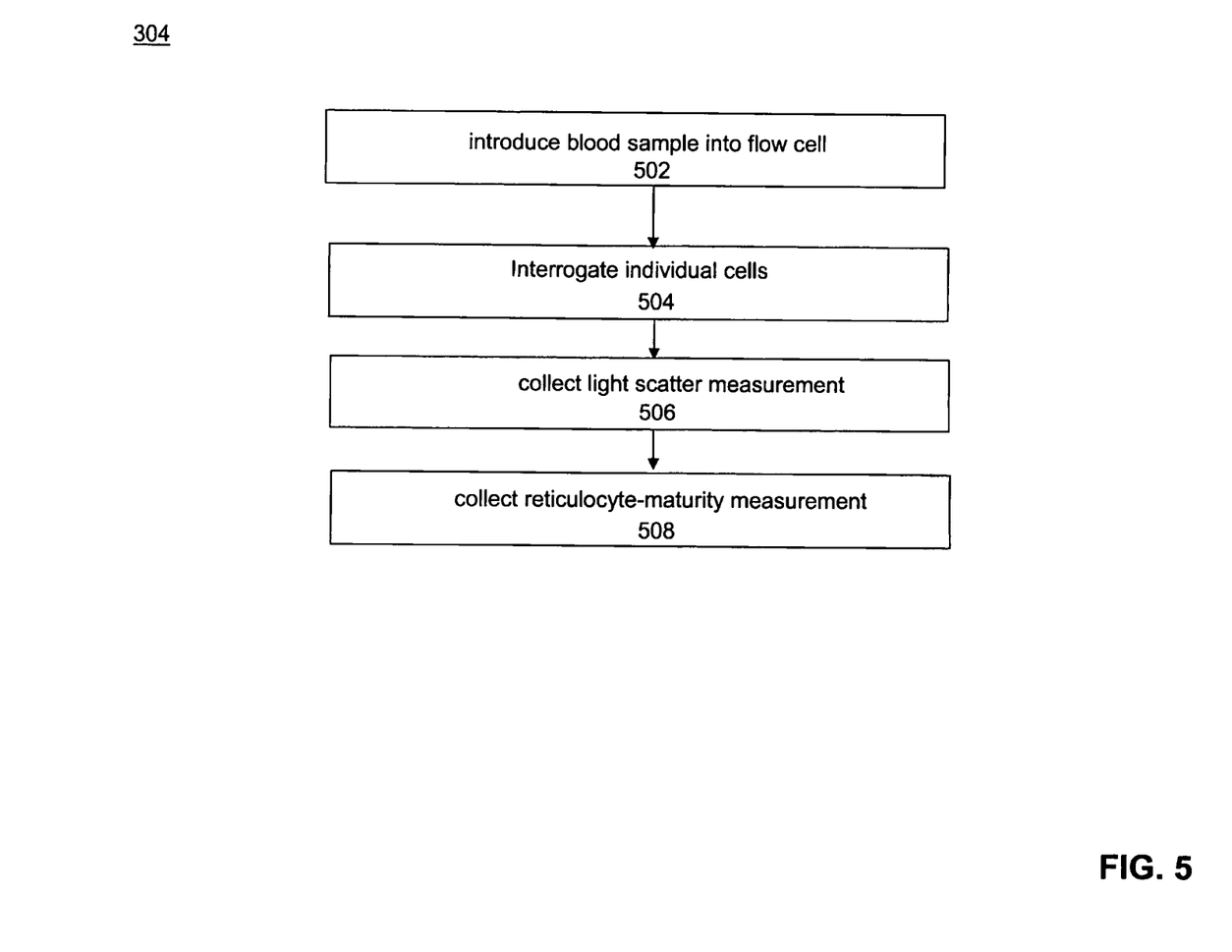
FIG. 5 shows further details of the measuring step shown in FIG. 3, according to an embodiment of the present invention.

Returning to FIG. 3, in step 304, the blood sample is analyzed using a particle analyzer. In one embodiment, the particle analyzer is a hematology analyzer. For example, the blood sample, or a portion of it, is introduced into the particle analyzer. Under hydrodynamic pressure, the blood sample flows, cell by cell, through a flow cell. Within the flow cell, the individual cells are interrogated by one or more probes including light beams. For example, in particle analyzers using the VCS technology, separate probes may interrogate the cell for volume, conductivity, and scatter. Several measurements may be collected per cell event. For example, side scatter, forward scatter, and fluorescence, are some measurements that are generally collected. FIG. 5 is a flowchart of step 304 in further detail, according to an embodiment of the present invention.

In step 502, the blood sample prepared in step 302, is introduced into a flow cell for analysis. In step 504, the sample is interrogated by probes including a laser as it flows, cell by cell, through an interrogation point in the flow cell. In step 506, the light scatter measurement is recorded for each cell event. The light scatter measurement may comprise of side scatter and forward scatter. The side scatter measurement represents the amount of light reflected laterally to the sides, due to structures in the cell that is being interrogated. In reticulocytes, the reflecting structure within the cell is generally the RNA. As it is known that in reticulocytes the amount of RNA contained is, in general, inversely proportional to the maturity of the reticulocyte, the side scatter measurement is expected to increase as the reticulocytes go from older to younger and the RNA content increases. Several measurements of side scatter may be available, for example, and without limitation, lower median angle light scatter (LMALS) and upper median angle light scatter (UMALS). The LMALS refers to light scattered at an 10°-20° angle from the axis of the beam, and UMALS refers to light scattered at an 20°-65° angle from the axis of the beam. Another side scatter measurement, side angle light scatter (SALS), may measure all light scattered at 90°-20° angle. Forward scatter measures the light that passes through the cell being interrogated and that is only deflected, for example, less than 20° from the axis of the beam of light. Axial light loss (ALL) is the amount of light lost at 0° relative to the axis of the beam. As the RNA content decreases with the maturity of the reticulocyte, it can be expected that the axial light loss measurement decreases.

In step 508, another measurement that is indicative of reticulocyte maturity is collected. For example, in one embodiment of the present invention, the size of the cell may be measured. The size of the cell is known to decrease with the maturity of the reticulocyte, in general, as the RNA content decreases. As an example, the size of the cell, or cell volume, may be measured using the DC measurement. The peak amplitude of the DC pulse is a function of cell volume. Other measurements indicative of reticulocyte maturity, including direct or indirect ways of measuring the volume of the cell, may be used in this step. For example, fluorescence measurement to indicate the amount of RNA in the cell, or other modes of measuring cell volume may be used. As another example, forward scatter may also be used to indicate cell size.

Returning again to FIG. 3, in step 306 a reticulocyte population is identified from the entire cell event population. Scatter plots of the event data, using various axis, help identify blood cell distribution patterns. As an example, the event data may be visualized in a scatter plot, such as, for example, FIG. 1, where the light scatter is on the x-axis and volume (DC) is on the y-axis. As indicated earlier with respect to FIG. 1, the reticulocyte population 104 can be identified separately from erythrocytes 102, platelets 108 and white cells 106. The accuracy of the reticulocyte population is dependent particularly on how definitively line 130 separating the reticulocytes from the red cells can be determined. For example, in one embodiment, while line 130 may be superimposed on the scatter plot 100 based on threshold light scatter and volume measurement values derived empirically from previous collections of measurements, line 130 may fail to correctly separate erythrocytes 102 from reticulocytes (104), particularly with regard to cell events that lie in close proximity to line 130 in scatter plot 100.

In step 308, an embodiment of the present invention determines immature reticulocytes using the light scatter measurement as well as a second reticulocyte maturity measurement, for example, DC. The use of two dimensions, both of which are indicative of reticulocyte maturity improves the accuracy of the reticulocyte measurements reported. For example, the method described above with respect to FIG. 2 differentiates immature reticulocytes based only on the light scatter measurement. This disclosure teaches how a second dimension can be used to increase the accuracy of the differentiation. The intent in this disclosure is to map reticulocyte events to two measurements indicative of reticulocyte maturity, and thereby obtain more accurate classification of the immature reticulocytes.

Figure 6:
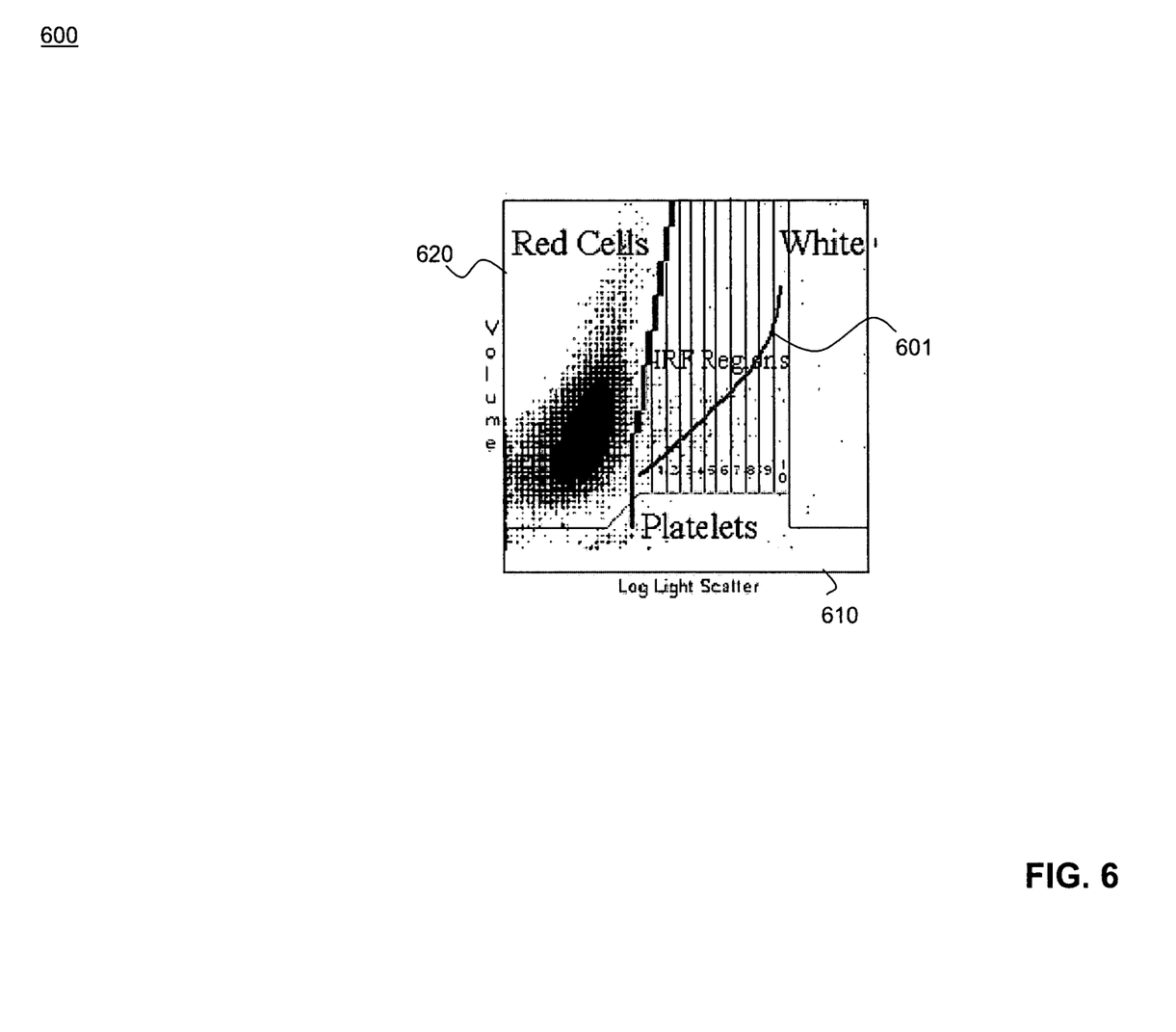
FIG. 6 shows a part of a method of evaluating immature reticulocytes, according to an embodiment of the present invention.

In an embodiment of the present invention, as shown in FIG. 6, a polynomial curve 601 representative of the distribution of average volume of reticulocytes is super-imposed on a scatter plot 600 having a light scatter axis 610 and a volume axis 620. The reticulocyte events are then mapped onto the polynomial curve. For example, for each point on polynomial curve 601, all reticulocyte cell events that are proximate to a line drawn perpendicular to curve 601 are mapped to that point. Thereafter, polynomial curve 601 is divided to 10 areas of equal length, and for each such area, all reticulocyte cell events contained are summed. Mapping reticulocyte events to the polynomial curve permits the creation of a histogram representing the distribution of reticulocyte events along the curve. Unlike histograms of earlier systems that classify reticulocyte events based on a light scatter axis, the histogram based on the polynomial curve 601 considers two dimensions that vary with reticulocyte maturity. Thus, when, for example, the immature reticulocyte fraction is computed based on the histogram using polynomial curve 601, both measurements are reflected in that quantification.

Figure 7:
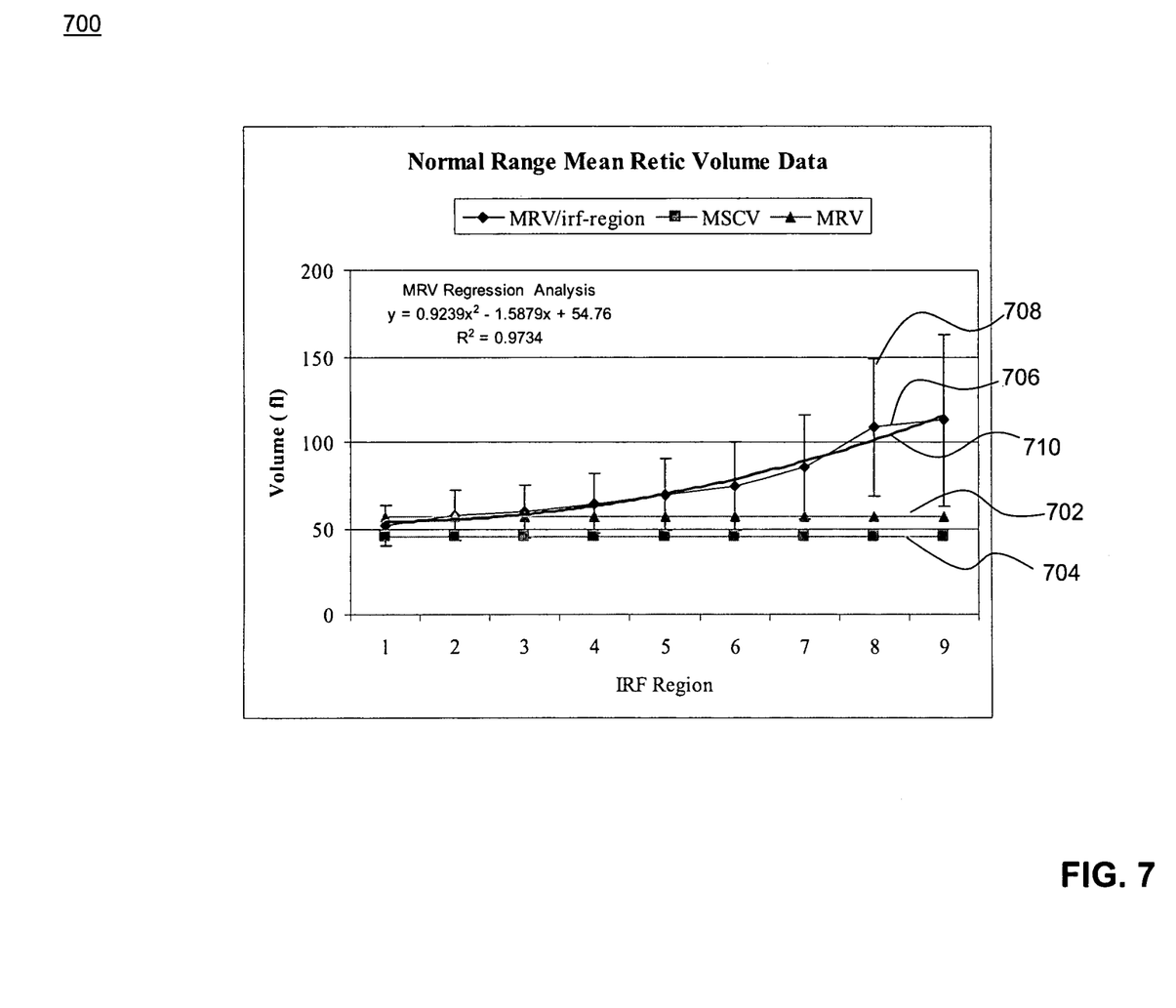
FIG. 7 shows the relationship of the mean reticulocyte volume to several other measurements, and the development of a curve representing average reticulocyte volume, in one embodiment of the present invention.

The mapping may take many forms. In one embodiment, the mapping can be based on a polynomial curve 601 as described above. Polynomial curve 601 (or more generally, the polynomial function corresponding to curve 601) was developed based on a substantial collection of experimental reticulocyte data. The sample data used for generating the polynomial 710 shown in FIG. 7, is based on 90 patient samples run on the Gen•S™ hematology analyzer. Reticulocyte events from each sample were classified into 10 IRF regions based on light scatter, for example, as shown in FIG. 2. Then for each of the 10 regions, the average cell volume was determined. The mean reticulocyte volume (MRV), and the mean sphered cell volume (MSCV) may also be determined. The MRV is determined as the mean DC value for the reticulocyte population. The MSCV is the mean DC value for the red cell population including the reticulocyte population. Graph 700 indicates that, as expected, the MSCV 704 is slightly lower than the MRV 702. More significantly, graph 700 shows the average volume of reticulocytes 706 in each region. The error bars attached to each average reticulocyte value, for example, error bar 708 of region 8, is indicative of the standard deviation of the reticulocyte volumes in that region. The standard deviation can be a function of the number of events analyzed. For example, in the set of samples analyzed in FIG. 7, the first region which corresponds to the region with the most mature reticulocytes, had 65000 events, whereas the outermost region had only 9 events in the entire sample. Overall, the average value reflects the trend of smaller reticulocyte volumes as the level of reticulocyte maturity increases. Using the data from this sample, a polynomial 710 was developed to fit the average value points 706.

$$\text{Polynomial curve 710 can be represented as: } y=ax^2+bx+c \qquad (1)$$

where a=0.9239, b=−1.5879, and c=54.76. The curve defined by equation (1) can be super-imposed on a reticulocyte region in order to map the events therein, to equation (1).

Returning yet again to FIG. 3, in step 310, one or more reticulocyte measures can be reported. In one embodiment the immature reticulocyte fraction is reported as the ratio of a predetermined number of regions defined on the mapping function to the entire reticulocyte population. In another embodiment immature reticulocytes may be reported as a percentage or absolute number. The regions can be defined based on the polynomial curve 710. For example, the immature reticulocyte fraction may be reported as the number of reticulocyte events that mapped to the leftmost 8 regions that were defined upon the polynomial curve 601, divided by the total reticulocyte events in the reticulocyte region. Reporting involves outputting one or more measurements to a display or other output device such as a computer file.

Removing "Hard-To-Ghost" Cells

The accuracy of reticulocyte maturity information that are reported, for example, the immature reticulocyte fraction, can improve with having more accurate sample data based on which to compute maturity information. It has been observed, in some blood samples, that after the initial ghosting process some cells remain that were either not ghosted or were only partially ghosted, i.e., "unghosted" cells. The ghosting process, for example, by combining a hypotonic acid solution with the blood sample, is intended to clear hemoglobin from the cells. Without ghosting or with inefficient ghosting, erythrocytes may not clearly differentiate from reticulocytes. The cells that prove resistant to ghosting are referred to as hard-to-ghost cells. Hard-to-ghost cells are particularly common in patients with some diseases, such as, for example, some varieties of the disease Thalassemia.

When hard-to-ghost cells are present in the blood sample, and the blood sample is analyzed using light scatter, as done at present, the differentiation of the reticulocytes from the mature red cells may fail because the hard-to-ghost cell population is dense and is generally positioned within the reticulocyte region.

Figure 8A:
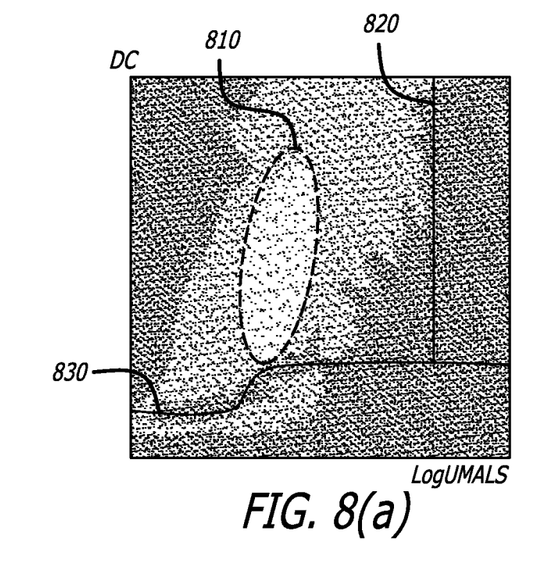
FIG. 8 is a two-dimensional view of event data from the analysis of a blood sample.
Figure 8B:
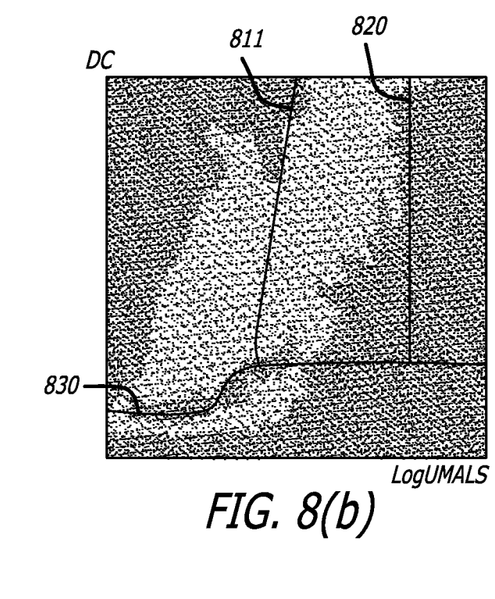

FIGS. 8(a) and 8(b) show the contrast presented in scatter plots of the same event data with and without hard-to-ghost cell events, using conventional light scatter or upper medium angle light scatter (UMALS) and DC axis. In FIG. 8(a) the scatter plot includes hard-to-ghost cell events. The boundary 810 shows the location of a hard-to-ghost cell event population. FIG. 8(b) shows the same event population after hard-to-ghost cell events, including the population defined by boundary 810, are removed. In both FIGS. 8(a) and 8(b), the events below boundary 830 correspond to platelets and the events to the right of boundary 820 correspond to white blood cells. As can be seen by the location of the boundary 810, the hard-to-ghost cell event population spans the separation of the mature red blood cell population and the reticulocyte population, thereby making it difficult to clearly distinguish between mature red blood cells and reticulocytes. In contrast, when the hard-to-ghost cell event population is removed, as shown in FIG. 8(b), a clear boundary 811 can be defined between the mature red blood cells and reticulocytes. A visual comparison of FIGS. 8(a) and 8(b) illustrates the difficulty in identifying and separating the mature red cells from reticulocytes when hard-to-ghost cells are present.

Figure 9:
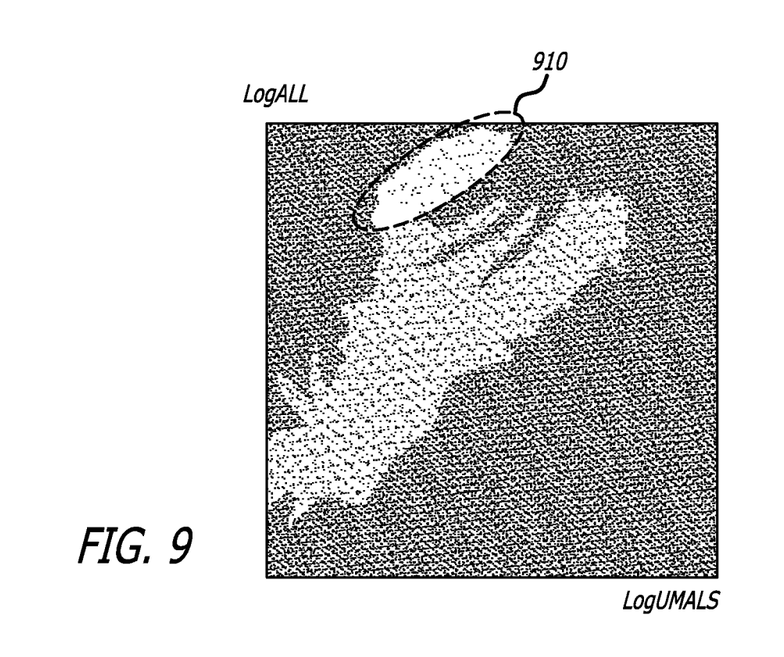
FIG. 9 is a view of the event data shown in FIG. 8, after "hard-to-ghost" cell population has been filtered-out.
Figure 10:
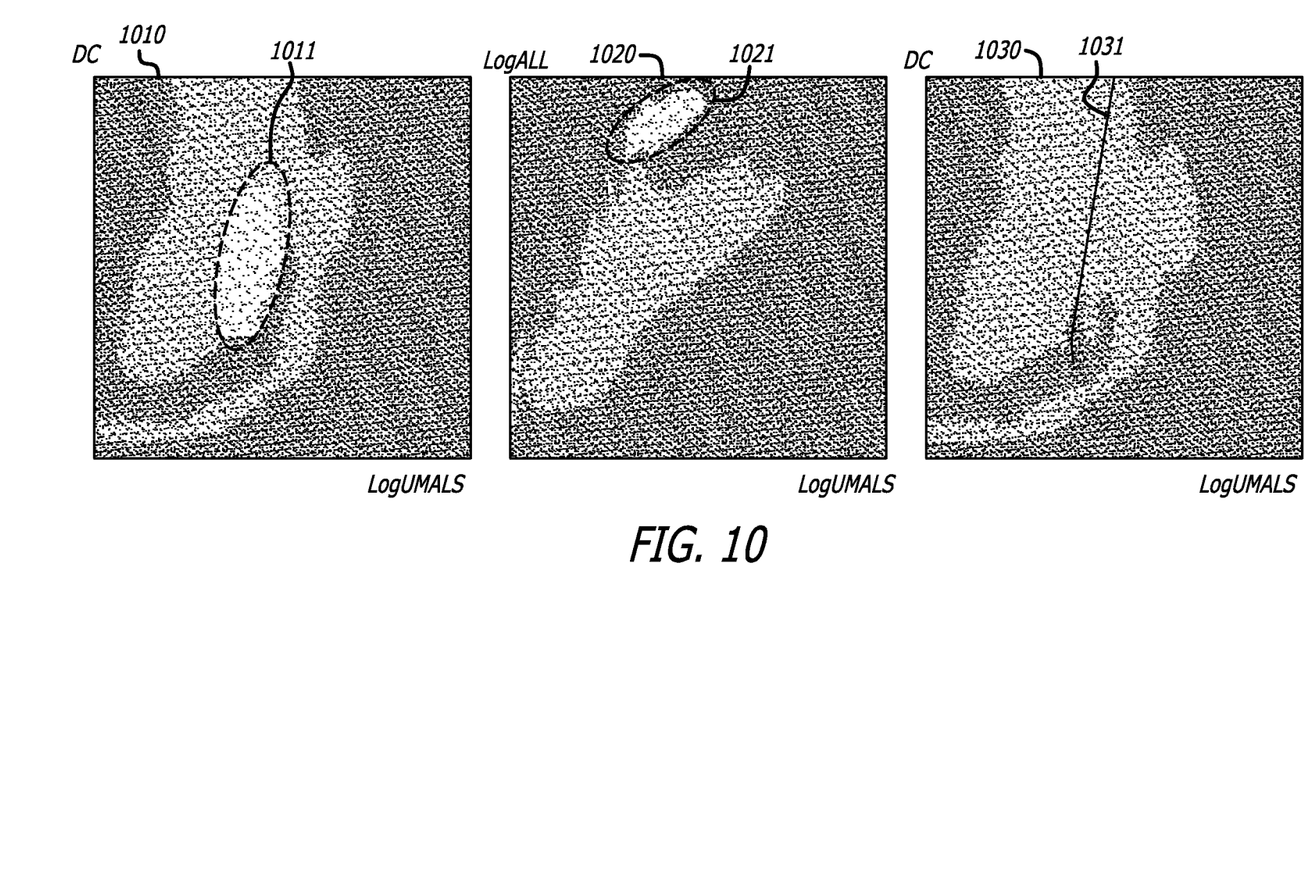
FIG. 10 shows several two-dimensional views illustrating event data with varying capability to identify the hard-to-ghost cell population.

In this embodiment of the present invention, the axial light loss measurement enables the discrimination of the hard-to-ghost population from the rest of the sample. For example, the same event population that cannot identify the hard-to-ghost population based on the conventionally used light scatter measurement, can now distinguish the population using an axial light loss measurement. For example, FIG. 9 shows the same event population shown in FIG. 8(a), but using axial light loss (ALL) and UMALS instead of the conventional DC and UMALS. Using ALL, hard-to-ghost cell events can be clearly identified, as shown by the area within the boundary 910. FIG. 10 illustrates the hard-to-ghost cell event removal of another blood sample using ALL in an embodiment of the present invention. Scatter plot 1010 shows the generally used UMALs and DC as axis. In scatter plot 1010, hard-to-ghost cells are present (as shown within boundary 1011), but cannot be clearly distinguished from other red blood cells. However, when the same data is shown in scatter plot 1020, having axial light loss (ALL) and UMALS as axis, the ability to differentiate is vastly improved. Based on ALL, the hard-to-ghost population 1021 is clearly discernible from the other event populations. Once the cell events corresponding to the hard-to-ghost population are filtered-out, the remaining cell events are displayed in scatter plot 1030 using the generally used UMALS axis and DC axis. Filtering-out cell events corresponding to the hard-to-ghost population may be accomplished by gating the hard-to-ghost population either, automatically based on, for example, threshold ALL and UMALS values determined empirically, or with manual operator assistance. A visual comparison of scatter plots 1030 and 1010 illustrates the clearer distinction between the mature red blood cell population to the left of boundary 1031 and the reticulocyte population to the right of boundary 1031.

As shown in FIG. 9 (specifically the area within boundary 910) and FIG. 10 (specifically the area within boundary 1021), when using ALL, hard-to-ghost cells can be identified as a distinct population from other populations such as mature red blood cells, reticulocytes, platelets and white blood cells. The hard-to-ghost cells generally display a higher ALL than other blood cell types except for white blood cells. White blood cells can be distinguished due to their high light scatter measurements relative to other blood cell types. The high ALL of the hard-to-ghost cell population can be attributed to the relatively high light absorption of hemoglobin. At a laser wavelength of 488 nm (the wavelength used in the particle analyzer that yielded results shown in FIGS. 8(a), 8(b), 9 and 10) hemoglobin displays very high optical absorption that leads to a high level of ALL. In general, hemoglobin shows increased absorption of light when the light is between 400-500 nm wavelength. Optical absorption of hemoglobin is illustrated in Prahl, Scott, "Optical Absorption of Hemoglobin," at http://omlc.ogi.edu/spectra/hemoglobin/index (Oregon Medical Laser Center, last accessed on Jul. 31, 2008).

Figure 11:
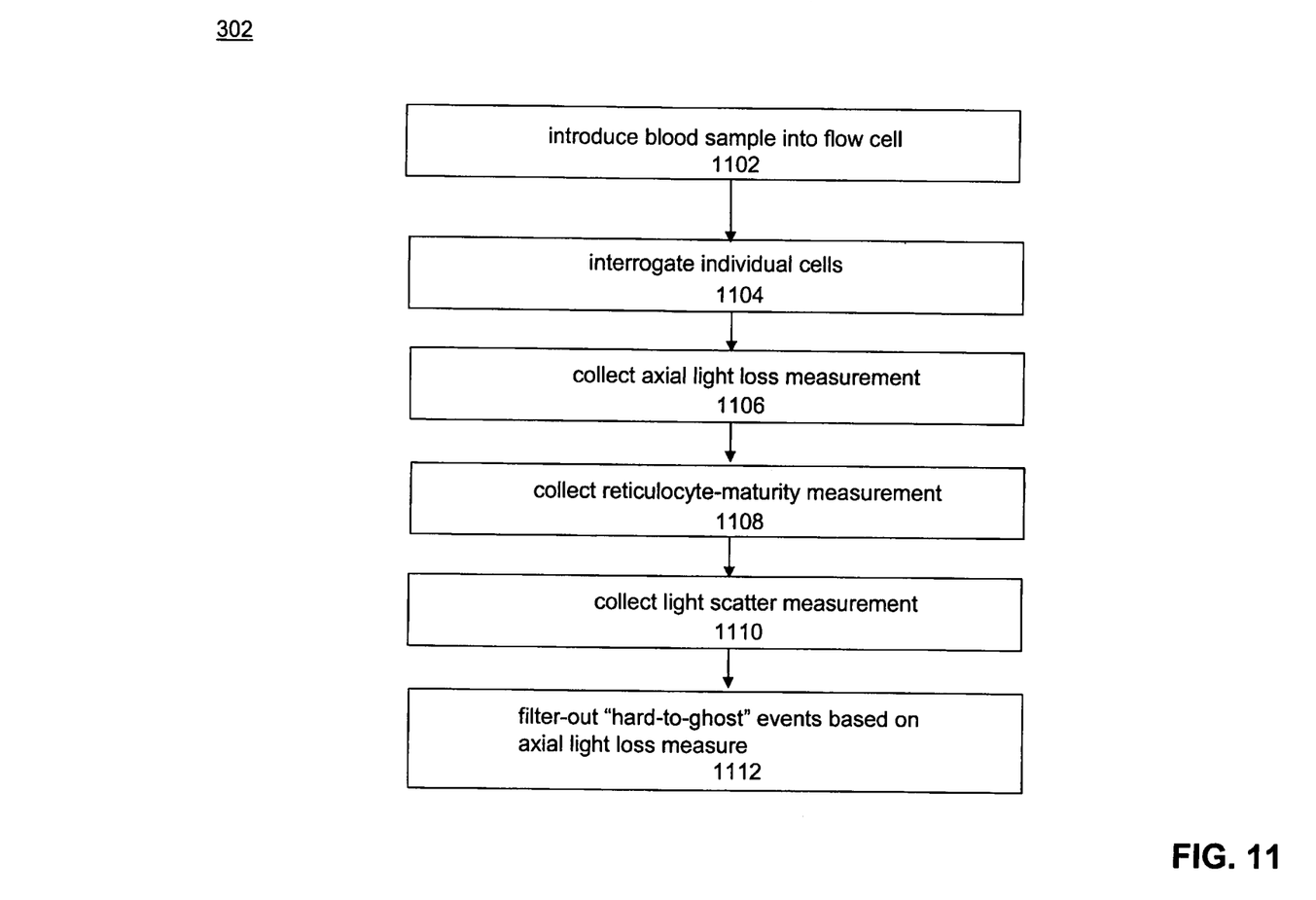
FIG. 11 shows further details of the measuring step shown in FIG. 3, according to another embodiment of the present invention.

When hard-to-ghost cells are expected to be present in a blood sample being analyzed, the embodiment of the present invention shown in FIG. 11 may be used. In FIG. 11, step 302 of FIG. 3 is further dissected to include steps to remove hard-to-ghost cells. In step 1102, a prepared blood sample, i.e., a sample having been ghosted and stained, can be introduced to a flow cell for analysis. In step 1104, the sample is interrogated, cell by cell, using probes including a light beam as explained with respect to FIG. 3 above. In step 1106, the ALL measurement is collected, along with a reticulocyte-maturity measurement in step 1108 and one or more other light scatter measurements in step 1110. Descriptions of the reticulocyte-maturity measurement and light scatter measurement can be found above with respect to FIG. 3. Having collected event data for the blood sample, here including the ALL measurement, in step 1112, the hard-to-ghost cell population is filtered out using the ALL values of the reticulocyte events.

When the hard-to-ghost cells have been removed from the sample population, the event data is available for further analysis for determining reticulocyte information or any other red cell information. In general, the removal of the hard-to-ghost cell event population would increase the accuracy of most parameters reported concerning red blood cells and/or reticulocytes. Calculation and reporting of reticulocyte information is described above with respect to FIG. 3.

System to Determine Reticulocyte Information

Figure 12:
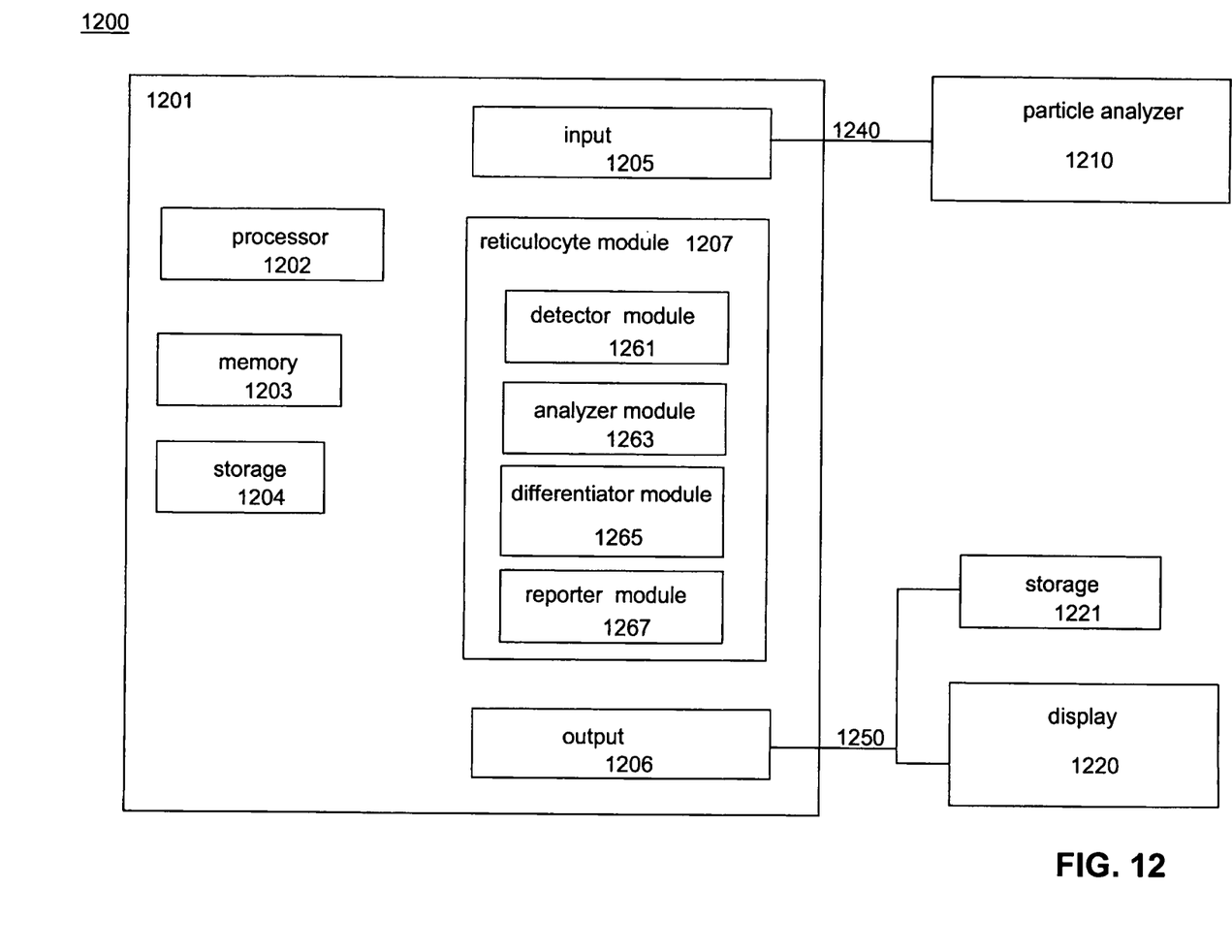
FIG. 12 is a system for evaluating immature reticulocytes according to an embodiment of the present invention.

FIG. 12 shows a system to evaluate reticulocytes in blood samples according to an embodiment of the present invention. A particle analyzer 1210 is coupled using link 1240 to a computer 1201. Computer 1201 is optionally coupled using link 1250 to a display 1220, and/or an external storage device 1221. Computer 1201 may include a processor 1202, a memory 1203, an internal storage 1204, an input module 1205, an output module 1206, and a reticulocyte module 1207. Reticulocyte module 1207 may include a detector module 1261, an analyzer module 1263, a differentiator module 1265, and a reporter module 1267.

Particle analyzer 1210 may include a hematology analyzer, flow cytometer, or similar device that is capable of interrogating a blood sample with the use of a beam of light. A blood sample is prepared an input to particle analyzer 1210 for analysis. The event data generated by particle analyzer 1210 is communicated to computer 1201, over the link 1240. Link 1240 can be a device-internal connection such as peripheral component interconnect (PCI) bus, or a network connection. The events generated by the analysis of blood samples in particle analyzer 1210 may be communicated to computer 1201 in real-time or in batch-mode.

The event data, subsequent to any processing within computer 1101, is then presented to a user on display 1220, or stored in external storage device 1221. For example, scatter plots generated by processing within computer 1201 may be presented to the user using display 1220. Processed event data may also be stored for later analysis and display. External storage device 1221 may include a hard drive, or other type of portable storage.

Processor 1202 may execute instructions that enable the processing of modules 1205, 1206 and 1207. Internal memory 1203 provides the temporary memory required for such processing, and internal storage 1204 may provide for the temporary or intermediate storage of data and results associated with such processing. Internal storage 1204 may also store control logic based on instructions and/or program code of modules including the component modules of reticulocyte module 1207, in the forms including computer readable program code.

Input module 1205 receives the event data generated by particle analyzer 1210. Input module 1205 may include any processing that is required to transform the input event data from particle analyzer 1210, to a format understood by reticulocyte module 1207. Output module 1206 collects the event data processed by reticulocyte module 1207, performs any conversion necessary, and outputs to either display 1220 or storage 1220, using link 1250. Link 1250 may be an device-internal connection such as PCI, or a network connection. Display 1220 may be a display device that is customized for the viewing of particle analyzer data, a generic display, or any other means capable of outputting results of the particle analysis.

The detector module 1261 may include the instructions for determining measurements or parameters of cell events as they pertain to side scatter including UMALS, forward scatter, axial light loss, and DC. Note that every embodiment of the present invention may not have access to all of the measurements above. There may be some configuration required on particle analyzer 1210 to enable the collection of all of the above measurements.

Analyzer module 1263 includes the instructions for identifying the reticulocyte population, isolating that population from other types of blood cells. In another embodiment, analyzer module 1263 may include instructions to filter-out the cell events corresponding to hard-to-ghost cells, as explained above.

Differentiator module 1265 may include instructions that cause the computer to determine the immature reticulocyte information of the sample being analyzed. For example, the reticulocyte event population identified using module 1263, may now be investigated using both, the light scatter measurement as well as a second reticulocyte maturity measurement such as volume, to differentiate the mature from the immature reticulocytes.

Reporter module 1267 includes the instruction enabling computer 1201 to display scatter plots to display 1220, and also to report useful quantifications of the reticulocytes in the blood sample. The reticulocyte fraction or the reticulocyte percentage are some quantifications that may be reported by reporter module 1267.

In this disclosure, methods were disclosed that can improve the accuracy of blood sample analysis through measures such as the immature reticulocyte fraction. The disclosed methods yield substantial improvements over the current methods and can lead to significant improvements in the detection and treatment of several diseases including Thalassemia. Persons skilled in the art will understand that the techniques disclosed herein can be applicable for cell types other than erythrocytes as described here.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of analyzing immature reticulocytes in a blood sample comprising:
   (a) measuring the cell volume and the light scatter of cells in the blood sample using a flow cell to generate particle data in volume—light scatter parameter space;
   (b) analyzing, using a computer, blood cell distribution patterns from the particle data to identify a set of particles corresponding to a population of reticulocytes in the blood sample;
   (c) generating a polynomial curve defining the relationship between reticulocyte volume and reticulocyte immaturity for a plurality of blood samples from a population of individuals and dividing the resulting polynomial curve into a plurality of segments, each segment corresponding to a reticulocyte maturity level;
   (d) mathematically superimposing, using the computer, the polynomial curve onto the blood cell distribution patterns in volume—light scatter parameter space corresponding to the population of reticulocytes in the blood sample;
   (e) mapping, using the computer, the set of reticulocyte particles in volume-light-scatter parameter space onto the polynomial curve using the shortest distance from the location of the reticulocyte particle in volume—light scatter parameter space to the polynomial curve by assigning each particle to the nearest segment of the polynomial curve;
   (f) counting the number of particles assigned to each segment of the polynomial curve to create a distribution of reticulocyte particles along the polynomial curve segments, thereby differentiating immature reticulocytes from mature reticulocytes; and
   (g) reporting immature reticulocytes in the blood sample.

2. The method of claim 1, further comprising exposing the blood sample to a vital stain to delineate reticulocytes.

3. The method of claim 1, further comprising exposing the blood sample to a ghosting reagent to remove hemoglobin from red blood cells.

4. The method of claim 1, wherein the light scatter measurement is a side scatter measurement or a forward scatter measurement.

5. The method of claim 1, wherein the volume measurement includes a direct current impedance measurement.

6. The method of claim 1, wherein reporting immature reticulocytes includes reporting a ratio of immature reticulocytes to total reticulocytes.

7. The method of claim 1, wherein the polynomial curve represents the distribution of average cell volume superimposed on a reticulocyte region of a scatter plot having a light scatter axis and a volume axis.

8. The method of claim 1, wherein the polynomial curve represents the distribution of mean reticulocyte volume superimposed on a reticulocyte region of a scatter plot having a light scatter axis and a volume axis.

9. The method of claim 1, wherein the polynomial curve represents the distribution of mean sphered cell volume superimposed on a reticulocyte region of a scatter plot having a light scatter axis and a volume axis.

10. The method of claim 1 wherein the polynomial curve is a quadratic polynomial curve.

11. The method of claim 1 wherein step (g) comprises reporting a ratio of the reticulocyte particles in a predetermined number of segments of the polynomial curve to the entire number of reticulocyte particles.

12. The method of claim 11 wherein the polynomial curve is divided into ten segments and the predetermined number of segments is eight and wherein the eight segments are the eight segments representing the eight most mature sets of reticulocytes.

* * * * *